(12) United States Patent
Cara et al.

(10) Patent No.: US 10,695,424 B2
(45) Date of Patent: Jun. 30, 2020

(54) METHOD OF MAKING A LIPOSOME COMPOSITION

(71) Applicant: GLAXOSMITHKLINE BIOLOGICALS S.A., Rixensart (BE)

(72) Inventors: Philippe Cara, Rixensart (BE); Veronique Monique Roberte Henderickx, Rixensart (BE); Vinciane Martha De Cupere, Rixensart (BE); Carine Berthe Ghislaine De Kesel, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 16/466,094

(22) PCT Filed: Dec. 5, 2017

(86) PCT No.: PCT/EP2017/081546
§ 371 (c)(1),
(2) Date: Jun. 3, 2019

(87) PCT Pub. No.: WO2018/104313
PCT Pub. Date: Jun. 14, 2018

(65) Prior Publication Data
US 2020/0061186 A1   Feb. 27, 2020

(30) Foreign Application Priority Data

Dec. 7, 2016  (GB) .................................. 1620758.1
Jun. 1, 2017  (GB) .................................. 1708734.7

(51) Int. Cl.
*A61K 39/39*   (2006.01)
*A61K 9/127*   (2006.01)
*A61K 39/00*   (2006.01)

(52) U.S. Cl.
CPC ............ *A61K 39/39* (2013.01); *A61K 9/1277* (2013.01); *A61K 2039/55555* (2013.01); *A61K 2039/55572* (2013.01); *A61K 2039/55577* (2013.01)

(58) Field of Classification Search
None
See application file for complete search history.

(56) References Cited

U.S. PATENT DOCUMENTS

2012/0093921 A1* 4/2012 Henderickx ........... A61K 39/00
                                                    424/450

FOREIGN PATENT DOCUMENTS

| WO | 1998015287 A1 | 4/1998 |
| WO | 2000007621 A2 | 2/2000 |
| WO | 2005112991 A2 | 12/2005 |
| WO | 2010142686 A1 | 12/2010 |
| WO | 2013041572 A1 | 3/2013 |

OTHER PUBLICATIONS

Brunner, Livia et al: "QS-21 Adjuvant: Laboratory-Scale Purification Method and Formulation Into Liposomes", Oct. 8, 2006 (Oct. 8, 2006), Methods in Molecular Biology, Humana Press, Inc, US, pp. 73-86.

* cited by examiner

*Primary Examiner* — Nannette Holloman
(74) *Attorney, Agent, or Firm* — Birch, Stewart, Kolasch & Birch, LLP (57) ABSTRACT

The present invention provides compositions, methods and processes for the maturation of submicron liposome compositions comprising a lipid, a sterol, and a saponin.

31 Claims, 8 Drawing Sheets
Specification includes a Sequence Listing.

SEQUENCE LISTING

<160> NUMBER OF SEQ ID NOS: 1

<210> SEQ ID NO 1
<211> LENGTH: 546
<212> TYPE: PRT
<213> ORGANISM: Artificial
<220> FEATURE:
<223> OTHER INFORMATION: Truncated gE from Varicella-Zoster virus

<400> SEQUENCE: 1

Met Gly Thr Val Asn Lys Pro Val Val Gly Val Leu Met Gly Phe Gly
1 5 10 15

Ile Ile Thr Gly Thr Leu Arg Ile Thr Asn Pro Val Arg Ala Ser Val
20 25 30

Leu Arg Tyr Asp Asp Phe His Ile Asp Glu Asp Lys Leu Asp Thr Asn
35 40 45

Ser Val Tyr Glu Pro Tyr Tyr His Ser Asp His Ala Glu Ser Ser Trp
50 55 60

Val Asn Arg Gly Glu Ser Ser Arg Lys Ala Tyr Asp His Asn Ser Pro
65 70 75 80

Tyr Ile Trp Pro Arg Asn Asp Tyr Asp Gly Phe Leu Glu Asn Ala His
85 90 95

Glu His His Gly Val Tyr Asn Gln Gly Arg Gly Ile Asp Ser Gly Glu
100 105 110

Arg Leu Met Gln Pro Thr Gln Met Ser Ala Gln Glu Asp Leu Gly Asp
115 120 125

Asp Thr Gly Ile His Val Ile Pro Thr Leu Asn Gly Asp Asp Arg His
130 135 140

Lys Ile Val Asn Val Asp Gln Arg Gln Tyr Gly Asp Val Phe Lys Gly
145 150 155 160

Asp Leu Asn Pro Lys Pro Gln Gly Gln Arg Leu Ile Glu Val Ser Val
165 170 175

Glu Glu Asn His Pro Phe Thr Leu Arg Ala Pro Ile Gln Arg Ile Tyr
180 185 190

Gly Val Arg Tyr Thr Glu Thr Trp Ser Phe Leu Pro Ser Leu Thr Cys
195 200 205

Thr Gly Asp Ala Ala Pro Ala Ile Gln His Ile Cys Leu Lys His Thr
210 215 220

Thr Cys Phe Gln Asp Val Val Val Asp Val Asp Cys Ala Glu Asn Thr
225 230 235 240

Lys Glu Asp Gln Leu Ala Glu Ile Ser Tyr Arg Phe Gln Gly Lys Lys
245 250 255

Glu Ala Asp Gln Pro Trp Ile Val Val Asn Thr Ser Thr Leu Phe Asp
260 265 270

Glu Leu Glu Leu Asp Pro Pro Glu Ile Glu Pro Gly Val Leu Lys Val
275 280 285

Leu Arg Thr Glu Lys Gln Tyr Leu Gly Val Tyr Ile Trp Asn Met Arg
290 295 300

Gly Ser Asp Gly Thr Ser Thr Tyr Ala Thr Phe Leu Val Thr Trp Lys
305 310 315 320

Gly Asp Glu Lys Thr Arg Asn Pro Thr Pro Ala Val Thr Pro Gln Pro
325 330 335

Arg Gly Ala Glu Phe His Met Trp Asn Tyr His Ser His Val Phe Ser
340 345 350

Val Gly Asp Thr Phe Ser Leu Ala Met His Leu Gln Tyr Lys Ile His

```
                355                 360                 365
Glu Ala Pro Phe Asp Leu Leu Leu Glu Trp Leu Tyr Val Pro Ile Asp
        370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Ile Arg Tyr Ala Ala Trp Thr Gly Gly
    530                 535                 540

Leu Ala
545
```

METHOD OF MAKING A LIPOSOME COMPOSITION

TECHNICAL FIELD

The present invention relates to improved processes for the production of saponin containing liposome compositions, in particular, filtration of such compositions.

BACKGROUND TO THE INVENTION

During the last few decades, liposomes (also known as bilayer lipid vesicles) are increasingly being used to encapsulate and deliver pharmaceutical compounds. Liposomes comprise one or more lipid (such as phospholipid), bilayers and can contain other molecules, such as proteins or carbohydrates, in their structure. The lipidic layer on the liposome confines and protects the enclosed pharmaceutical compound until the liposome reaches its destination and adheres to the outer membrane of targeted cells. By this process, drug toxicity to healthy cells is minimized and therapeutic efficacy can be increased. Due to the presence of both lipid and aqueous phases in their structure, liposomes can be utilized in the encapsulation or entrapment of water- and lipid-soluble material in addition to amphiphilic compounds.

Liposomes can be used in vaccine/immunogenic compositions in the formulation of adjuvant compositions. As these adjuvant compositions are often parenterally administered to humans, it is desirable that these are sterile. Liposomes used as adjuvants are generally submicron liposomes and are sufficiently small to be sterile-filtered through 0.2 μm filters. It is an object of the present invention to provide a process for improved filtration of submicron liposomes.

SUMMARY OF THE INVENTION

The present inventors improved filtration of saponin containing submicron liposomes using methods involving maturing the submicron liposomal formulations. Accordingly, the present invention provides a method of making a composition comprising a saponin in a submicron liposomal formulation, comprising the steps of:
a. preparing a first submicron liposomal formulation wherein the liposomes contain a lipid and a sterol,
b. adding the saponin to the first submicron liposomal formulation,
c. maturing the saponin containing submicron liposomal formulation for at least 1, at least 2, at least 3, at least 4, at least 5, at least 6, at least 7, at least 8, at least 9, at least 10, at least 11, at least 12, at least 13, at least 14, at least 15, or, at least 16 hours, and,
d. filtering the matured saponin containing submicron liposomal formulation of step c. through a sterile grade filter.

In another aspect, the present invention provides a a method of making a liposome composition comprising a saponin in a submicron liposomal formulation wherein the liposomes contain a lipid and a sterol, comprising the steps of:
a) maturing a saponin containing submicron liposomal formulation wherein the liposomes contain a lipid and a sterol for at least 1, at least 2, at least 3, at least 4, at least 5, at least 6, at least 7, at least 8, at least 9, at least 10, at least 11, at least 12, at least 13, at least 14, at least 15, or at least 16 hours, and,
b) filtering the matured saponin containing submicron liposomal formulation of step a) through a sterile grade filter.

In a further aspect, the invention provides a method for preparing a vaccine composition comprising preparing a liposome composition according to the method described herein whereby the liposome composition is combined with an antigen, either prior to or after the filtering of step d. of the method.

A method for preparing a vaccine kit comprising preparing a liposome composition according to the method described herein and packaging the liposome composition into a kit as a kit component in addition to an antigen kit component.

DESCRIPTION OF THE FIGURES

FIG. 3: Illustration of the evolution of particle size (nm) of saponin containing liposomal formulation lot 1 (A) and lot 2 (B) at different maturation times for Example 3.

FIG. 4: Illustration of the evolution of PDI of saponin containing liposomal formulation lot 1 (A) and lot 2 (B) at different maturation times for Example 3.

FIG. 5: Illustration of Vmax on three different lots of filter of saponin containing liposomal formulation lot 1 (A) and lot 2 (B) at different maturation times for Example 3.

FIG. 6: Illustration of cholesterol content (μg/ml) before and after filtration on three different lots of filter of saponin containing liposomal formulation lot 1 (A) and lot 2 (B) at different maturation times for Example 3.

DETAILED DESCRIPTION OF THE INVENTION

Liposomes, particularly submicron liposomes can be used in the formulation of immunological adjuvants. Vaccine compositions comprising said liposomes in combination with one or more antigens, are usually administered parenterally and thus it is desirable for the liposome compositions to be sterile. The present inventors have shown surprisingly that a maturation step (as defined in the next section) resolves/avoids problems in filtration of the liposomes, such as clogging of the filter.

Accordingly, the present invention provides a method of making a composition comprising a saponin in a submicron liposomal formulation wherein the liposomes contain a lipid and a sterol, comprising the steps of:
a. preparing a first submicron liposomal formulation wherein the liposomes contain a lipid and a sterol,
b. adding the saponin to the first submicron liposomal formulation,
c. maturing the saponin containing submicron liposomal formulation for at least 1, 2, 3, 4, 5, 6, 7, 8, 9, 10, 11, 12, 13, 14, 15, or, at least 16 hours, and,
d. filtering the matured saponin containing submicron liposomal formulation of step c. through a sterile grade filter.

Maturation

By "maturation" or "maturing" it is meant that the saponin containing submicron liposomal composition is stored for at least 1, 2, 3, 4, 5, 6, 7, 8, 9, 10, 11, 12, 13, 14, 15, or at least 16 hours following addition of the saponin to the first submicron liposomal composition. In one embodiment, maturation lasts for at least 4 hours, at least 6 hours or at least 8 hours. In one embodiment, maturation will be applied or performed for no longer than 36 hours, no longer than 48 hours, or, no longer than 24 hours. In a further embodiment, maturation is applied for a time between 4 and 24 hours. In a further embodiment, maturation is applied or performed for 16 to 24 hours. Maturation can be performed in any suitable container. In an embodiment, maturation is performed without stirring the formulation. After a formulation has undergone one or more maturation or maturing step(s), it may be described as "matured."

Maturation is performed at any suitable temperature. Typically, maturation is performed at room temperature, at a temperature between 15 and 30° C., or, at a temperature between 15 and 25° C. Alternatively, maturation is performed at about 18, 19, 20, 21, 22, 23, 24, 25, 26, or 27° C.

In one embodiment, maturation is done at a temperature between 15 and 25° C. for a period of 8 to 24 hours.

Sterilisation

By "sterile grade filter" it is meant a filter that produces a sterile effluent after being challenged by microorganisms at a challenge level of greater than or equal to $1 \times 10^7/cm^2$ of effective filtration area. Sterile grade filters are well known to the person skilled in the art of the invention and typically have a pore size of about 0.2 μm, and thus include filters with a pore size of about 0.22 μm. For the purpose of the present invention, sterile grade filters have a pore size between 0.1 and 0.25 μm, such as between 0.18 and 0.22 μm.

The membranes of the sterile grade filter can be made from any suitable material known to the skilled person, for example, but not limited to cellulose acetate, polyethersulfone (PES), polyvinylidene fluoride (PVDF), polytetrafluoroethylene (PTFE), and the like. In a particular embodiment of the invention, one or more or all of the filter membranes of the present invention comprise polyethersulfone (PES), in particular hydrophilic polyethersulfone. In a particular embodiment of the invention, the filters used in the processes described herein are a double layer filter, in particular a sterile filter with build-in prefilter having larger pore size than the pore size of the end filter. In one embodiment the sterilizing filter is a double layer filter wherein the pre-filter membrane layer has a pore size between 0.3 and 0.5 μm, such as 0.35 or 0.45 μm. According to further embodiments, filters comprise asymmetric filter membrane(s), such as asymmetric hydrophilic PES filter membrane(s). Alternatively, the sterilizing filter layer may be made of PVDF, e.g. in combination with an asymmetric hydrophilic PES pre-filter membrane layer.

Liposomes

The term 'liposome' is well known in the art and defines a general category of vesicles which comprise one or more lipid bilayers surrounding an aqueous space. Liposomes thus consist of one or more lipids, such as phospholipid, bilayers and can contain other molecules, such as proteins or carbohydrates, in their structure. Because both lipid and aqueous phases are present, liposomes can encapsulate or entrap water-soluble material, lipid-soluble material, and/or amphiphilic compounds. The liposomes intended for the present invention contain a substantial amount of (liposome forming) lipids. Liposome forming lipids are available in the art, and may be anionic, cationic or neutral lipids. In one embodiment, the liposome forming lipid portion consists essentially of neutral lipid. By "neutral lipid" is understood that the overall net charge of the lipid is (approximately) zero. The lipid may therefore be non-ionic overall or may be zwitterionic. In one embodiment, the liposomes comprises a zwitterionic lipid. Examples of suitable lipids are phospholipids such as phosphatidylcholine species. In one embodiment, the liposomes contain phosphatidylcholine as a liposome forming lipid which is suitably non-crystalline at room temperature. Examples of such non-crystalline phosphatidylcholine lipids include egg yolk phosphatidylcholine, dioleoyl phosphatidylcholine (DOPC) or dilauryl phosphatidylcholine (DLPC). In a particular embodiment, the liposomes of the present invention contain DOPC, or, consist essentially of DOPC.

The liposomes may also contain a limited amount of a charged lipid which increases the stability of the liposome-saponin structure for liposomes composed of saturated lipids, e.g. liposomes composed of DLPC. In these cases, the amount of charged lipid is suitably 1-20% w/w, preferably 5-10% w/w of the liposome composition. Suitable examples of such charged lipids include fatty acids such as lauric acid, or alternatively, phosphatidylglycerol and phosphatidylserine. Suitably, the neutral liposomes will contain less than 5% w/w charged lipid, such as less than 3% w/w or less than 1% w/w. In a particular embodiment, the liposomes are composed of DLPC and lauric acid, e.g. in a ratio DLPC:Lauric acid between 3.5:1 and 4.5:1, such as about 4:1.

The liposomes intended for the present invention further comprise a sterol. Suitable sterols include β-sitosterol, stigmasterol, ergosterol, ergocalciferol and cholesterol. In one particular embodiment, the liposomes comprise cholesterol as sterol. These sterols are well known in the art, for example cholesterol is disclosed in the Merck Index, 11th Edn., page 341, as a naturally occurring sterol found in animal fat. The ratio of sterol to lipid is typically 1:100 to 1:2 (mol/mol), suitably 1:5 to 1:4, or about 1:4.

In a specific embodiment, the liposomes of the present invention comprise DOPC and cholesterol in a 1:4 ratio (cholesterol:DOPC)

Z-average diameter (ZAD) and polydispersity index (PDI) are determined on the basis of data obtained by dynamic light scattering (DLS). A monochromatic and coherent laser light beam illuminates a representative sample for particle size analysis, dispersed in a liquid at a suitable concentration. The light scattered by the particles at a given angle is recorded by a detector (an avalanche photodiode) whose output is fed to a correlator. Since the dispersed particles are in continuous Brownian motion, the observed scattered intensity fluctuates along the time axis. Therefore, analysis as a function of time of these intensity fluctuations provides information on the motion of the dispersed particles. In a DLS experiment, the time analysis is carried out with a correlator which constructs the time autocorrelation function of the scattered intensity. The decay rate is linked to the translational diffusion coefficient D of the particles. This decay is interpreted in terms of average particle size and polydispersity index by the so-called cumulants method.

For non-interacting spherically shaped particles dispersed in a medium of viscosity η, the diffusion coefficient D is related to the particle hydrodynamic diameter dH by the Stokes-Einstein equation:

$$D = \frac{kT}{3\pi\eta d_H}$$

where
k is the Boltzmann constant,
T the absolute temperature
η the viscosity of the medium.

The cumulants method is a simple method of analysing the autocorrelation function generated by a DLS experiment. The calculation is defined in ISO 13321 and ISO 22412. The first two terms of this moments expansion are used in practice, a mean value for the size (z-average size or z-average mean or z-average diameter), and a width parameter known as the polydispersity index (PDI).

Z-Average Size

The z-average size is an intensity-based calculated value and should not be confused with or directly compared to a mass or number mean value produced by other methods. The calculation is defined in the ISO standards, so all systems that use this calculation as recommended should give comparable results if the same scattering angle is used.

The z-average size or z-average mean or z-average diameter used in dynamic light scattering is a parameter also known as the cumulants mean. It is the primary and most stable parameter produced by the technique. The z-average mean is commonly used in a quality control setting as is defined in ISO 13321 and more recently ISO 22412 which defines this mean as the 'harmonic intensity averaged particle diameter'.

The z-average size will only be comparable with the size measured by other techniques if the sample is monomodal (i.e. only one peak), spherical or near-spherical in shape, monodisperse (i.e. very narrow width of distribution), and the sample is prepared in a suitable dispersant, as the z-average mean size can be sensitive to even small changes in the sample, e.g. the presence of a small proportion of aggregates. It should be noted that the z-average is a hydrodynamic parameter and is therefore only applicable to particles in a dispersion or molecules in solution.

Submicron liposomes have an average diameter of less than 1 μm. Methods of measuring liposome diameter are well known to the skilled person e.g. dynamic light scattering. For the purpose of description of the present invention, the average diameter of the liposomes is expressed as Z-average diameter (ZAD).

Liposomes of the invention can have an average diameter between about 30 and 300 nm, between 50 and 225 nm, between 50 and 200 nm, between 80 and 200 nm, between 80 and 150 nm, or between 80 and 120 nm. Alternatively, the average diameter of the liposomes can be about 30, 40, 50, 75, 100, 125, 150, 175, 200, 225, 250, 275 and 300 nm. In one embodiment, liposomes produced by the methods of the invention have an average diameter between 50 to 150 nm. The average diameter of the liposomes can be affected, for example, by extrusion of the liposomal composition through sieves or meshes with a known pore size. This and further methods of controlling the size of liposomes are well known in the art and are described, for example, in Mayhew et al (1984) Biochim. Biophys. Acta 775:169-174 or Olson et al (1979) Biochim. Biophys. Acta 557:9-23. In a particular embodiment of the invention, liposomes have an average diameter (ZAD) of less than about 220 nm, less than 200 nm, in particular between about 50 nm and about 150 nm, in particular between about 80 nm and 120 nm.

Polydispersity Index

This index is a number calculated from a simple 2 parameter fit to the correlation data (the cumulants analysis). The polydispersity index is dimensionless and scaled from 0 to 1. The very small values (e.g., 0.05) correspond to highly monodisperse standards. The closer the values to 1, the broader the size distribution of the particles.

The polydispersity index (PDI) of a liposomal formulation is a measure of the heterogeneity of liposome particles in the formulation. In an embodiment, the PDI of the liposomal formulation following maturation of step c. is below 0.225. In a further embodiment, PDI is below 0.200.

Saponins

In the method of the invention, there is provided the step of adding a saponin to the liposomal formulation following preparation of the 20 submicron liposomes and prior to the maturation step.

A particularly suitable saponin for use in the present invention is Quil A and its derivatives. Quil A is a saponin preparation isolated from the South American tree Quillaja Saponaria Molina and was first described by Dalsgaard et al. in 1974 ("Saponin adjuvants", Archiv. für die gesamte Virusforschung, Vol. 44, Springer Verlag, Berlin, p243-254) to have adjuvant activity. Purified fragments of Quil A have been isolated by HPLC which retain adjuvant activity without the toxicity associated with Quil A (EP 0 362 279), for example QS7 and QS21 (also known as QA7 and QA21). QS21 is a natural saponin derived from the bark of Quillaja saponaria Molina, which induces CD8+ cytotoxic T cells (CTLs), Th1 cells and a predominant IgG2a antibody response and is a particular saponin in the context of the present invention.

In particular, the saponins for use in the present invention are immunologically active fractions of Quil A, such as QS-7 or QS21, suitably QS21. In a specific embodiment, QS21 is provided in its less reactogenic composition where it is quenched with an exogenous sterol, such as cholesterol for example, for example a sterol such as cholesterol that is incorporated in the liposomal formulation. The ratio of QS21:sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). The sterol is suitably cholesterol.

Buffers

The liposomal formulation may contain a buffer. Also, the method of the invention may comprise a further step of adding buffer to the first liposomal formulation. The buffers used in the present invention include: a phosphate buffer (Na/Na$_2$PO$_4$, Na/K$_2$PO$_4$ or K/K$_2$PO$_4$); a Tris buffer; a borate buffer; a succinate buffer; a histidine buffer; or a citrate buffer. Buffers will typically be included in an amount between 5 and 20 mM. In a particular embodiment, the buffer is phosphate buffered saline (PBS). The pH of the liquid mixture is adjusted in view of the therapeutic components of the composition. Suitably, the pH of the liquid mixture is at least 4, at least 5, at least 5.5, at least 5.8, at least 6. Alternatively stated, the pH of the liquid mixture may be less than 9, less than 8, less than 7.5 or less than 7. In other embodiments, pH of the liquid mixture is between 4 and 9, between 5 and 8, between 5.5 and 7.5, or, between 5.8 and 6.4. In a specific embodiment, the pH is about 6.1.

Tonicity

Solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the immunogenic compositions of the present invention will have an osmolality in the range of 250 to 750 mOsm/kg, for example, the osmolality may be in the range of 250 to 550 mOsm/kg, such as in the range of 280 to 500 mOsm/kg. Osmolality may be measured according to techniques known in the art, such as by the use of a commercially available osmometer, for example the Advanced® Model 2020 available from Advanced Instruments Inc. (USA).

Tonicity of the composition may be adjusted using methods known to the skilled person such as by providing appropriate amounts of isotonifying agents. An "isotonicity agent" or "isotonifying agent" is a compound that is physiologically tolerated and imparts a suitable tonicity to a formulation (e.g. immunogenic compositions of the invention) to prevent the net flow of water across cell membranes that are in contact with the formulation. Aqueous adjuvant compositions are known which contain 100 mM sodium chloride or more, for example adjuvant system A (ASA) in WO 2005/112991 and WO2008/142133 or the liposomal adjuvants disclosed in WO2007/068907.

In some embodiments, the isotonicity agent used for the composition is a salt, such as sodium chloride. In other embodiments, however, the composition comprises a non-ionic isotonicity agent and the concentration of sodium chloride or the ionic strength in the composition is less than 100 mM, such as less than 80 mM, e.g. less than 30 mM, such as less 10 mM or less than 5 mM. The composition may comprise a non-ionic isotonicity agent and conductivity of the composition is less than 5 mS/cm, such as less than 4 mS/cm. In a preferred embodiment, the non-ionic isotonicity agent is a polyol, such as sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2012/080369 and WO2012/080370 which are incorporated herein by reference.

Preparation of the Submicron Liposome Composition

Processes for preparing the first submicron liposomal formulation of step a. are available in WO2013/041572 (also published as US20140234403, incorporated herein by reference in its entirety), in particular examples 3 and 4, describe methods for making a liposome preparation of DOPC liposomes further containing cholesterol and optionally 3D-MPL. The liposome preparation as described therein is further admixed with QS21.

In one embodiment, the liposomes obtained in step a. have been subjected to a homogenisation, or alternatively stated, step a. comprises homogenisation of the liposomal formulation, in particular high shear and/or high pressure homogenisation.

In another embodiment, step a. is done using a method of forming a lipidic film comprising the steps (i) dissolving a lipid mix in a solvent to a form a homogeneous mix; (ii) removing the solvent to form a lipidic film (e.g. by evaporation); (iii) hydrating the lipidic film with a hydrating solution to form a liposome composition; and (iv) reducing the size of liposome to form a submicron liposome composition (in particular by using high shear and/or high pressure homogenisation).

Homogenisation

In one embodiment of the invention, the liposomes are first pre-homogenised with a high shear mixer. This step is intended to reduce the size of the coarse liposomes. A rotor or impellor, together with a stationary component known as a stator, or an array of rotors and stators, is used either in a tank containing the solution to be mixed, or in a pipe through which the solution passes, to create shear. A high shear mixer can be used to create emulsions, suspensions, lyosols (gas dispersed in liquid) and granular products.

In one embodiment, the pre-homogenised liposomes are further homogenized with a high pressure homogenizer. This process is well known in the art and usually involves a standard homogeniser. The solution may be homogenised in the first reaction container or the solution may be transferred to a second reaction container before homogenising. Suitable reaction containers for use as the second reaction container can hold a volume of liquid and include, but are not limited to tanks, such as stainless steel tanks, flasks or beakers. In one embodiment, the liposome suspension is pressurised during homogenisation.

In one embodiment, the liposomes are homogenised using a high shear homogenizer in-line with a high pressure homogeniser. Such technology is well known in the art and homogenisation usually occurs in a range of pressure between 5000 and 30000 psi, i.e. 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000 or 30000 psi.

TLR-4 Agonist

In a further embodiment, the liposomal formulation further comprises a TLR-4 agonist. For example, this may be a detoxified lipopolysaccharide. The lipopolysaccharide is intended to function as an immunostimulant in liposomes generated using the methods of the inventions. In one embodiment, the lipopolysaccharide is a non-toxic derivative of lipid A, such as monophosphoryl lipid A or more particularly 3-Deacylated monophoshoryl lipid A (3D-MPL). 3D-MPL is sold under the name MPL by GlaxoSmithKline Biologicals S.A. and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-7 (Th1) phenotype.

3D-MPL can be produced according to the methods disclosed in GB2220211 A. Chemically it is a mixture of 3-deacylated monophosphoryl lipid A with 3, 4, 5 or 6 acylated chains. Mixtures containing greater than 20% of 6 acylated chains are preferred. In the compositions of the present invention, small particle 3D-MPL may be used. Small particle 3D-MPL has a particle size such that it can be sterile-filtered through a sterilizing filter such as one of the sterilizing filters described for the purpose of the invention. Such preparations are described in WO94/21292.

Other TLR-4 agonists which can be used are alkyl glucosaminide phosphates (AGPs) such as those disclosed in WO 98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR-4 agonists, and some are TLR-4 antagonists. Both are thought to be useful as adjuvants.

Other suitable TLR-4 ligands are as described in WO2003/011223 and in WO 2003/099195, such as compound I, compound II and compound III described on pages 4-5 of WO2003/011223 or on pages 3-4 of WO2003/099195 and in particular those compounds described in WO2003/011223 as ER803022, ER803058, ER803732, ER804053, ER804057m ER804058, ER804059, ER804442, ER804680 and ER804764. For example, one suitable TLR-4 ligand is ER804057.

Other TLR-4 ligands which may be of use in the present invention include Glucopyranosyl Lipid Adjuvant (GLA) such as described in WO2008/153541 or WO2009/143457 or the literature articles Coler R N et al. (2011) Development and Characterization of Synthetic Glucopyranosyl Lipid Adjuvant System as a Vaccine Adjuvant. PLoS ONE 6(1): e16333. doi:10.1371/journal.pone.0016333 and Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7(7): e41144. doi:10.1371/journal.pone.0041144. WO2008/153541 or WO2009/143457 are incorporated herein by reference for the purpose of defining TLR-4 ligands which may be of use in the present invention.

A TLR-4 ligand such as a lipopolysaccharide, such as 3D-MPL, can be used at amounts between 1 and 100 μg per human dose of the adjuvant composition. 3D-MPL may be used at a level of about 50 μg, such as at least 40 μg, at least 45 μg or at least 49 μg, or, less than 100 μg, less than 80 μg, less than 60 μg, less than 55 μg or less than 51 μg. Examples of suitable ranges are between 40-60 μg, suitably between 45-55 μg or between 49 and 51 μg or 50 μg. In a further embodiment, the human dose of the adjuvant composition comprises 3D-MPL at a level of about 25 μg, such as at least 20 μg, at least 21 μg, at least 22 μg or at least 24 μg, or, less than 30 μg, less than 29 μg, less than 28 μg, less than 27 μg or less than 26 μg. Examples of lower ranges include between 20-30 μg, suitably between 21-29 μg or between 22-28 μg or between 28 and 27 μg or between 24 and 26 μg, or 25 μg.

Packaging

Following sterile filtration, the sterile submicron liposome composition is packaged into suitable containers. The submicron liposome compositions may be packed into vials, in particular single dose glass vials. Alternatively, the submicron liposome compositions may be packed into bags such as high density polyethylene storage bags.

Methods of Preparing Vaccines

The present invention further provides methods for preparing vaccines comprising preparing a submicron liposome composition by the processes of the invention described herein and combining the liposome composition with an antigen.

The term 'antigen' is well known to the skilled person. An antigen can be a protein, polysaccharide, peptide, nucleic acid, protein-polysaccharide conjugates, molecule or hapten that is capable of raising an immune response in a human or animal. Antigens may be derived, homologous or synthesised to mimic molecules, from viruses, bacteria, parasites, protozoan or fungus. In an alternative embodiment of the invention the antigen is derived, homologous or synthesised to mimic molecules, from a tumour cell or neoplasia. In a further embodiment of the invention the antigen is derived, homologous or synthesised to mimic molecules, from a substance implicated in allergy, Alzheimer's disease, atherosclerosis, obesity and nicotine-dependence.

In a particular embodiment of the invention, the antigen is derived from *Plasmodium* spp, for example *P. falciparum* or *P. vivax*.

In a particular embodiment of the invention, the antigen is derived from *Mycobacterum* spp, for example *M. tuberculosis*.

Possible antigens derived from *Plasmodium falciparum* include circumsporozoite protein (CS protein), RTS, PfEMP-I, Pfs 16 antigen, MSP-I, MSP-3, LSA-I, LSA-3, AMA-I and TRAP. Other *P. falciparum* antigens include EBA, GLURP, RAPI, RAP2, Sequestrin, Pf332, STARP, SALSA, PfEXPI, Pfs25, Pfs28, PFS27/25, Pfs48/45, Pfs230 and their analogues in other *Plasmodium* spp. The antigen may be an entire protein or an immunogenic fragment thereof.

An antigen derived from *Plasmodium falciparum* CS protein may be in the form of a hybrid fusion protein. The fusion protein may contain protein derived from *P. falciparum* CS protein fused to another protein or fragment thereof. The fusion protein may contain an N-terminal or C-terminal fragment from the CS protein of *P. falciparum*. Alternatively, or in addition, the fusion protein may comprise one or more repeat units (e.g. 1, 2, 3, 4, 5, 6, 7, 8, 9 or more repeat units) from the central region of *P. falciparum* CS protein. In one embodiment, the fusion protein is a hybrid fusion protein comprising an antigen derived from CS protein together with a surface antigen from hepatitis B (HBsAg) or an immunogenic fragment thereof. Typically, the surface antigen from Hepatitis B comprises the major surface protein known as the S antigen, for example, S antigen derived from an adw serotype.

In particular, the fusion protein may comprise substantially all the C-terminal portion of the CS protein of *P. falciparum*, four or more tandem repeats of the CS protein immunodominant region, and the surface antigen from hepatitis B (HBsAg). In one aspect, the fusion protein comprises a sequence which contains at least 160 amino acids which is substantially homologous to the C-terminal portion of the CS protein. In particular, "substantially all" the C terminal portion of the CS protein includes the C terminus devoid of the hydrophobic anchor sequence. The CS protein may be devoid of the last 12 to 14 (such as 12) amino-acids from the C terminal.

In one embodiment, the fusion protein for use in the invention is a protein which comprises a portion of the CS protein of *P. falciparum* substantially as corresponding to amino acids 207 395 of *P. falaparum* 3D7 clone, derived from the strain NF54 (Caspers et al, supra) fused in frame via a linear linker to the N terminal of HBsAg. The linker may comprise part or all of the preS2 region from HBsAg.

A particular fusion protein for use in the invention is the fusion protein known as RTS, as described in WO 93/10152 and WO 98/05355. The RTS may be in the form of RTS,S mixed particles (wherein "S" represents an unfused monomer) or as RTS. The RTS,S particles comprise two polypeptides RTS and S that may be synthesized simultaneously and spontaneously form composite particulate structures (RTS,S) e.g. during purification. These particles may also be referred to a Virus Like Particles (VLP). Such particles can be prepared in a number of ways, for example by expressing the fusion protein in a suitable host such as yeast or bacteria.

It is believed that the presence of the surface antigen from Hepatitis B and the formation of the RTS,S particles boosts the immunogenicity of the CS protein portion of the hybrid protein, aids stability, and/or assists reproducible manufacturing of the protein.

The CS antigens may be used in conjunction with another antigen selected from any antigen which is expressed on the sporozoite or the pre-erythrocytic stage of the parasite life cycle such as the liver stage, for example liver stage antigen-1 (LSA-1), liver stage antigen-3 (LSA-3), thrombospondin related anonymous protein (TRAP), merozoite surface protein-1 (MSP1) the major merozoite surface protein, and apical merezoite antigen-1 (AMA-1). Other suitable antigens to use in conjunction with CS antigens include PfEMP-I, Pfs 16 antigen, MSP-3, LSA-3, AMA-I, TRAP, GLURP, RAPI, RAP2, Sequestrin, Pf332, STARP, SALSA, PfEXPI, Pfs25, Pfs28, PFS27/25, Pfs48/45, Pfs230.

Immunogenic fragments of any of the antigens as described herein will contain at least one epitope of the antigen and display malaria antigenicity and are capable of raising an immune response when presented in a suitable construct, such as for example when fused to other malaria antigens or other non-malaria antigens, or presented on a carrier, the immune response being directed against the native antigen. Typically, the immunogenic fragments contain at least 20, or at least 50, or at least 100 contiguous amino acids from the malaria antigen.

Possible antigens from *P. vivax* include circumsporozoite protein (CS protein) based antigens and Duffy antigen binding protein and fragments thereof, such as PvRII (see e.g. WO02/12292).

Possible CS protein based antigens may include a fusion protein comprising sequences derived from a CS protein of *P. vivax*. In one embodiment, the fusion protein is a hybrid fusion protein. The hybrid protein herein may contain protein derived from *P. vivax* type I and type II. In particular, the hybrid fusion protein may contain protein derived from *P. vivax* type I and type II fused to another protein or fragment thereof.

In one aspect, the hybrid fusion protein comprises a hybrid protein derived from the CS proteins of *P. vivax* (CSV) and a surface antigen from Hepatitis B, generally the major surface protein known as the S antigen, such as the S antigen derived from an adw serotype.

Preferably, the fusion protein is an immunogenic hybrid fusion protein comprising: a) at least one repeat unit derived from the central repeat section of a type I circumsporozoite protein of *P. vivax*, b) at least one repeat unit derived from the central repeating section of a type II circumsporozoite protein of *P. vivax*, and c. surface antigen S derived from Hepatitis B virus.

The CSV derived antigen component of the invention is generally fused to the amino terminal end of the S protein. More specifically the C-terminus end of the CSV fragment is fused the N-terminus of said S antigen. For example, a suitable fusion protein is CSV-S, as described in WO2008/009652.

In yeast cells, once expressed, the hybrid fusion protein (comprising S antigen), is able to spontaneously assemble into a lipoprotein structure/particle composed of numerous monomers of said proteins (or VLPs). Such particles can be prepared by expressing the fusion protein in a suitable host such as yeast or bacteria.

When the chosen recipient yeast strain also carries in its genome one or more integrated copies of a hepatitis B S expression cassette, the resulting strain synthesizes hybrid protein as a fusion proteins, and also non-fused S antigen. These may spontaneously be assembled into lipoprotein particles comprising monomers of the hybrid fusion protein and monomers of the S antigen.

Also provided, is a VLP comprising CSV-S and/or RTS units. The particle may consist essentially of CSV-S and RTS units. Alternatively, the particles produced comprise or consist essentially of CSV-S, RTS and S units. Such mixed particles are described for example in WO2008/009650.

Antigens of interest in the field of tuberculosis include Mtb72f and variants thereof, such as disclosed in WO2006/117240. An antigen of particular interest is M72, the polypeptide sequence of which being provided in SEQ ID No: 4 and a polynucleotide sequence encoding said polypeptide being provided in SEQ ID No: 3 of WO2006/117240.

A further antigen of interest in the field of tuberculosis is Rv1753 and variants thereof, such as disclosed in WO2010/010180, for example a Rv1753 sequence selected from SEQ ID Nos: 1 and 2-7 of WO2010/010180, in particular SEQ ID No: 1. Another antigen of interest in the field of tuberculosis is Rv2386 and variants thereof, such as disclosed in WO2010/010179, for example a Rv2386 sequence selected from SEQ ID Nos: 1 and 2-7 of WO2010/010179, in particular SEQ ID No: 1. Other antigens of interest in the field of tuberculosis include Rv3616 and variants thereof, such as disclosed in WO2011092253, for example a natural Rv3616 sequence selected from SEQ ID Nos: 1 and 2-7 of WO2011/092253 or a modified Rv3616 sequence such as those selected from SEQ ID Nos: 161 to 169, 179 and 180 of WO2011092253, in particular SEQ ID No: 167. An additional antigen of interest is HBHA, such as disclosed in WO97/044463, WO03/044048 and WO2010/149657.

Tuberculosis antigens are suitably utilised in the form of a polypeptide, but may alternatively be provided in the form of a polynucleotide encoding said polypeptide.

In a particular embodiment, methods of the invention use antigens derived from Varicella Zoster Virus (VZV). The VZV antigen for use in the invention may be any suitable VZV antigen or immunogenic derivative thereof, suitably being a purified VZV antigen. The term 'immunogenic derivative' encompasses any molecule which retains the ability to induce an immune response to VZV following administration to man.

Suitable methods for the generation of derivatives are well known in the art and include standard molecular biology techniques as disclosed, for example, in Sambrook et al [Molecular Cloning: A Laboratory Manual, third edition, 2000, Cold Spring Harbor Laboratory Press], such as techniques for the addition, deletion, substitution or rearrangement of amino acids or chemical modifications thereof. In one aspect derivatives include, for example, truncations or other fragments.

In one aspect, derivatives in the context of this invention are amino acid sequences comprising epitopes, i.e., antigenic determinants substantially responsible for the immunogenic properties of a polypeptide and being capable of eliciting an immune response, in one aspect being T cell epitopes.

In one aspect, the level of immunogenic activity of the immunogenic derivative is at least about 50%, in one aspect at least about 70% and in one aspect at least or greater than about 90% of the immunogenicity for the polypeptide from which it is derived, suitably as assessed by immunoassay techniques described above. In some aspects of the invention immunogenic portions may be identified that have a level of immunogenic activity greater than that of the corresponding full-length polypeptide, e.g., having greater than about 100% or 150% or more immunogenic activity. In one aspect, the VZV antigen is a glycoprotein, in one aspect the gE antigen (also known as gp1), or immunogenic derivative thereof.

The gE antigen, anchorless derivatives thereof (which are also immunogenic derivatives) and production thereof is described in EP0405867 and references therein [see also Vafai A. Antibody binding sites on truncated forms of varicella-zoster virus gpI (gE) glycoprotein Vaccine 199412: 1265-9]. EP192902 also discloses gE and production thereof.

In one aspect gE is a truncated gE having the sequence of Seq ID No. 1 herein, and as disclosed in Virus research, vol 40, 1996 p199 ff, herein incorporated fully by reference. Reference to gE hereinafter includes reference to truncated gE, unless otherwise apparent from the context.

Kits

The present invention further provides methods for preparing a vaccine kit comprising preparing submicron liposome compositions of the invention as described herein and packaging the liposome composition into a kit as a kit component in addition to an antigen kit component.

The antigen and/or liposomes may be prepared extemporaneously, at the time of delivery. Thus, the invention provides methods for preparing vaccine kits including an antigen and liposome composition ready for mixing. The kits allow the antigen and liposome composition to be kept separately until the time of use.

The components are physically separate from each other within a kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container (for example vial).

In a particular embodiment, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration. In another preferred arrangement, the two kit components are held together but separately in the same syringe e.g. a dual-chamber syringe. When the syringe is actuated (e.g. during administration to a patient) then the contents of the two chambers are mixed. This arrangement avoids the need for a separate mixing step at the time of use.

The kit components may be in aqueous form. In some embodiments, a component (such as the antigen) is in dry form (e.g. in a lyophilised form), with the other component (the liposome composition) being in aqueous form. The two components can be mixed in order to reactivate the dry component and give an aqueous composition for administration to a patient. A lyophilised component will typically be located within a vial rather than a syringe.

Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilised antigen component in a vial.

Embodiments herein relating to "vaccine compositions" of the invention are also applicable to embodiments relating to "immunogenic compositions" of the invention, and vice versa.

The singular terms "a," "an," and "the" include plural referents unless context clearly indicates otherwise. Similarly, the word "or" is intended to include "and" unless the context clearly indicates otherwise. The term "plurality" refers to two or more. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, or antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example." The open transitional phrase "comprising", "comprise" and "comprises" herein are intended by the inventors to be optionally substitutable with the closed transitional phrase "consisting of", "consist of" and "consists of", respectively, in every instance.

Additionally, numerical limitations given with respect to temperatures, percentages of, concentrations of, or levels of a substance, such as a composition, are intended to be approximate. Thus, where a temperature is indicated to be 15° C. to 25° C., it is intended that the temperature be understood to be approximately (or " " or "~") 15° C. to approximately (or " " or "~") 25° C. Likewise, a concentration is indicated to be at least (for example) 200 µg, it is intended that the concentration be understood to be at least approximately (or " " or "~") 200 µg. The term "about" in relation to a numerical value x means x±5% or x±10%.

Although methods and materials similar or equivalent to those described herein can be used in the practice or testing of this disclosure, suitable methods and materials are described below. The following examples illustrate the invention.

EXAMPLES

Example 1. Preparation of the Concentrated Liposome Bulk

The concentrated liposome bulk was prepared as described in example 3 of WO2013/041572 (incorporated herein by reference in its entirety). Briefly, the concentrated liposome bulk has been prepared in 2 steps. The first step was the lipidic film preparation. DOPC (Dioleoyl phosphatidylcholine), 3D-MPL and cholesterol were dissolved sequentially in isopropanol. Then isopropanol was stripped off under stirring and reduced pressure gradient in a warming bath at 55° C. to obtain a film residue. The pressure was then gradually reduced and a final drying was applied to obtain a lipidic film. The second step was the preparation of the concentrated liposomes bulk. To that end, the lipidic film was rehydrated in PBS to form a coarse suspension of liposomes. The liposome suspension was then homogenized with a high-shear mixer in-line with a high-pressure homogenizer to produce the desired nano-sized liposomes. The resulting concentrated liposome bulk (which does not comprise QS21) is filtered through a 0.22 µm PES membrane. The concentrated liposome bulk for use in the examples contained 40 mg/ml of DOPC, 10 mg/ml Cholesterol, 2 mg/ml MPL in 10 mM phosphate buffer (pH 6.1) and 150 mM NaCl.

Example 2. Preparation of the Saponin Containing Liposomes—Filterability

Figure 1:
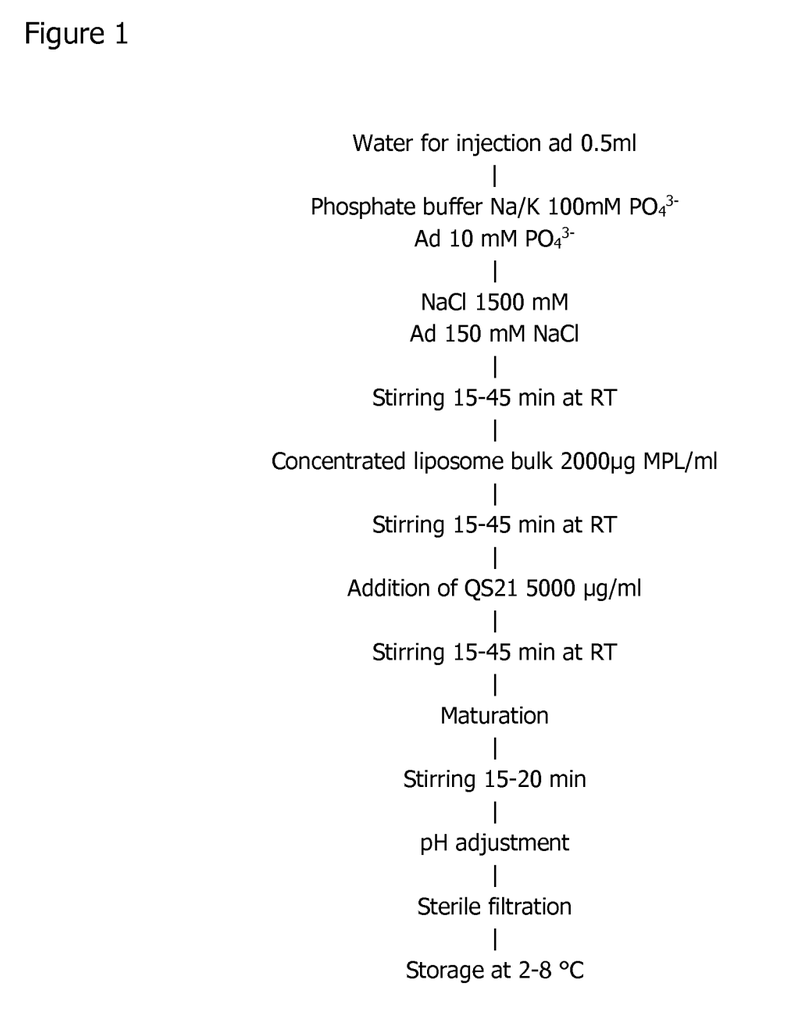
FIG. 1: Flow sheet illustrating the formulation of the saponin containing liposomal formulation of Example 2 and 3.

The purpose of the test was to evaluate filterability of the QS21 containing liposomal formulation after different maturation times (0 hours, ½ hours, 4 hours and 24 hours) and on different filters (Sartopore2 0.45-0.2 µm, Sartopore 2 XLI 0.35-0.2 µm, Sartopore XLG 0.8-0.2 µm, Pall EKV and Pall EDF). The liposomal formulation is prepared following the protocol as illustrated by the flow-sheet of FIG. 1. In summary, the addition of QS21 to the concentrated liposome bulk as prepared in Example 1, in appropriate buffer, results in the QS21 containing liposomal formulation to be subjected to the filterability evaluation, as described above. For the present test, the liposomal formulation used for filtration had the following composition:

| | |
|---|---|
| MPL | 100 µg/ml |
| Cholesterol | 500 µg/ml |
| DOPC | 2000 µg/ml |
| QS21 | 100 µg/ml |
| NaCl | 150 mM |
| $Na_2HPO_4$ | 2.1 mM |
| $KH_2PO_4$ | 7.9 mM |

Figure 2:
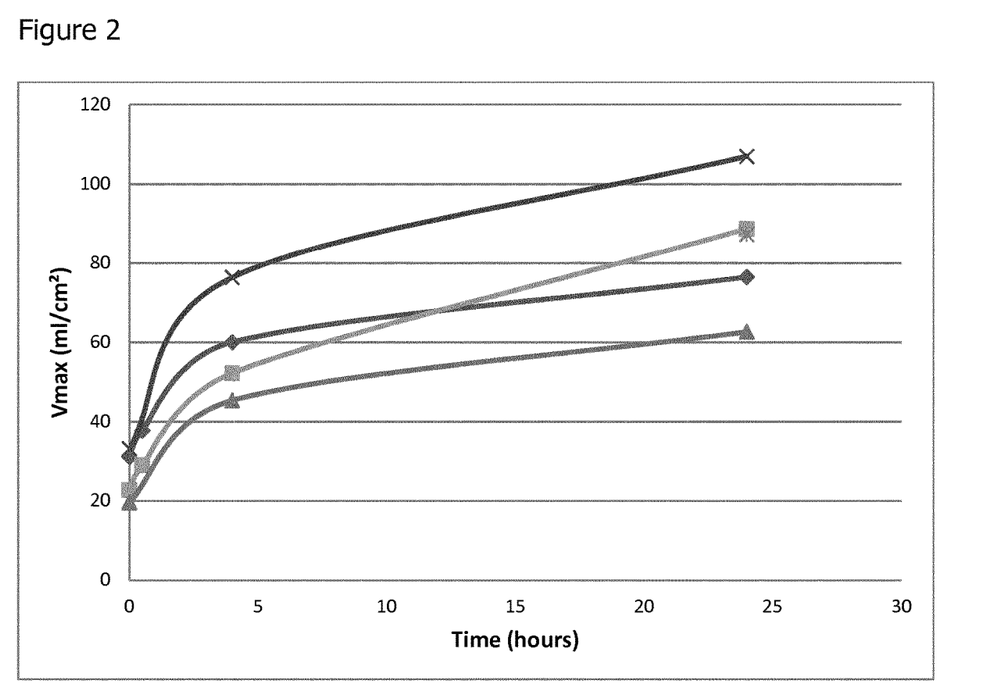
FIG. 2: Illustration of Vmax in function of time before filtration using different filters: ♦ Sartopore2 0.45/02; ■ Sartopore2 0.35/0.2; ▲ Sartopore2 0.8/0.2; ✕ Pall EKV; ✶ Pall EDF.

Filterability was tested at a pressure of 0.8 bar and measured as Vmax, i.e. the maximum volume that can be passed through the filter before blocking of the filter. The results obtained are listed in Table 1 and illustrated in FIG. 2.

TABLE 1

| Time before filtration (Maturation time) | Filter type | Vmax (ml/cm$^2$) |
|---|---|---|
| 0 hours | Sartopore2 0.45-0.2 μ | 31.2 |
| | Sartopore 2 XLI 0.35-0.2 μ | 22.8 |
| | Sartopore XLG 0.8-0.2 μ | 19.6 |
| | Pall EKV | 33.3 |
| ½ hours | Sartopore2 0.45-0.2 μ | 37.8 |
| | Sartopore 2 XLI 0.35-0.2 μ | 29.1 |
| 4 hours | Sartopore2 0.45-0.2 μ | 60.1 |
| | Sartopore 2 XLI 0.35-0.2 μ | 52.3 |
| | Sartopore XLG 0.8-0.2 μ | 45.4 |
| | Pall EKV 0.65-0.2 μ | 76.4 |
| | Sartopore2 0.45-0.2 μ | 62.2 |
| | Sartopore 2 XLI 0.35-0.2 μ | 52.9 |
| | Sartopore XLG 0.8-0.2 μ | 42 |
| 24 hours | Sartopore2 0.45-0.2 μ | 76.5 |
| | Sartopore 2 XLI 0.35-0.2 μ | 88.7 |
| | Sartopore XLG 0.8-0.2 μ | 62.7 |
| | Pall EKV | 107 |
| | Pall EDF | 87.3 |

Results

Irrespective of the type of filter used, the filterability of the QS21 containing liposomal composition increases over the maturation time, as displayed by the increase of Vmax according to the maturation time. The longer liposomes are matured, the higher Vmax is.

Example 3. Preparation of the Saponin Containing Liposomes—Particle Size, PDI, Vmax, MPL/QS21/DOPC/Cholesterol Content Two lots of QS21 containing liposomal formulation having the composition as detailed for Example 2, were also produced following the flow-sheet of FIG. 1. Three lots of Pall EKV filters (Pall 1, Pall 2 and Pall 3) were tested, without maturation (TO) and after 2 or 4 hours of maturation (T2H & T4H). The following parameters were measured:

Average particle size (nm) before and after maturation (ZAD)
PDI before and after maturation
Vmax (ml/m$^2$) on filtration
MPL, QS21, DOPC and Cholesterol content before and after filtration ZAD and PDI were measured in accordance with the ISO 13321 and ISO 22412 standards.

Table 2 lists the indicated contents measured at TO, T2H and T4H after filtration on the different lots of Pall EKV filters. A sample has also been collected before filtration to use as the reference content.

TABLE 2

| Maturation time (T) - Filter lot (Pall No.) | MPL (μg/ml) | QS21 (μg/ml) | DOPC (mg/ml) | Cholesterol (μg/ml) |
|---|---|---|---|---|
| Lot 1 | | | | |
| before filtration | 107 | 105 | 2 | 503 |
| T0 Vmax 1 - Pall 1 | 106 | 102 | 2 | 490 |
| T2 H Vmax 1 - Pall 1 | 105 | 102 | 2 | 495 |
| T4 H Vmax 1 - Pall 1 | 105 | 103 | 2 | 496 |
| T0 Vmax 2 - Pall 2 | 108 | 100 | 2 | 491 |
| T2 H Vmax 2 - Pall 2 | 104 | 103 | 2 | 500 |
| T4 H Vmax 2 - Pall 2 | 107 | 104 | 2 | 499 |
| T0 Vmax 3 - Pall 3 | 104 | 100 | 1.9 | 484 |
| T2 H Vmax 3 - Pall 3 | 107 | 102 | 2 | 499 |
| T4 H Vmax 3 - Pall 3 | 106 | 103 | 2 | 502 |
| Lot 2 | | | | |
| before filtration | 90 | 112 | 2 | 500 |
| T0 Vmax 1 - Pall 1 | 86 | 104 | 2 | 483 |
| T2 H Vmax 1 - Pall 1 | 87 | 107 | 2 | 496 |
| T4 H Vmax 1 - Pall 1 | 93 | 108 | 2 | 494 |
| T0 Vmax 2 - Pall 2 | 88 | 106 | 2 | 490 |
| T2 H Vmax 2 - Pall 2 | 96 | 108 | 2 | 491 |
| T4 H Vmax 2 - Pall 2 | 103 | 110 | 2 | 497 |
| T0 Vmax 3 - Pall 3 | 85 | 106 | 2 | 483 |
| T2 H Vmax 3 - Pall 3 | 92 | 108 | 2 | 489 |
| T4 H Vmax 3 - Pall 3 | 102 | 109 | 2 | 492 |

Results

Irrespective of the filter lot, with both lots of QS21 containing liposomal formulations, there is no substantial variation in the contents measured after a maturation time of 2h or 4h (and after filtration), as compared with the contents measured before filtration. This indicates that no loss of content with regard to MPL, QS21, DOPC and cholesterol happened after maturation.

Figure 3:
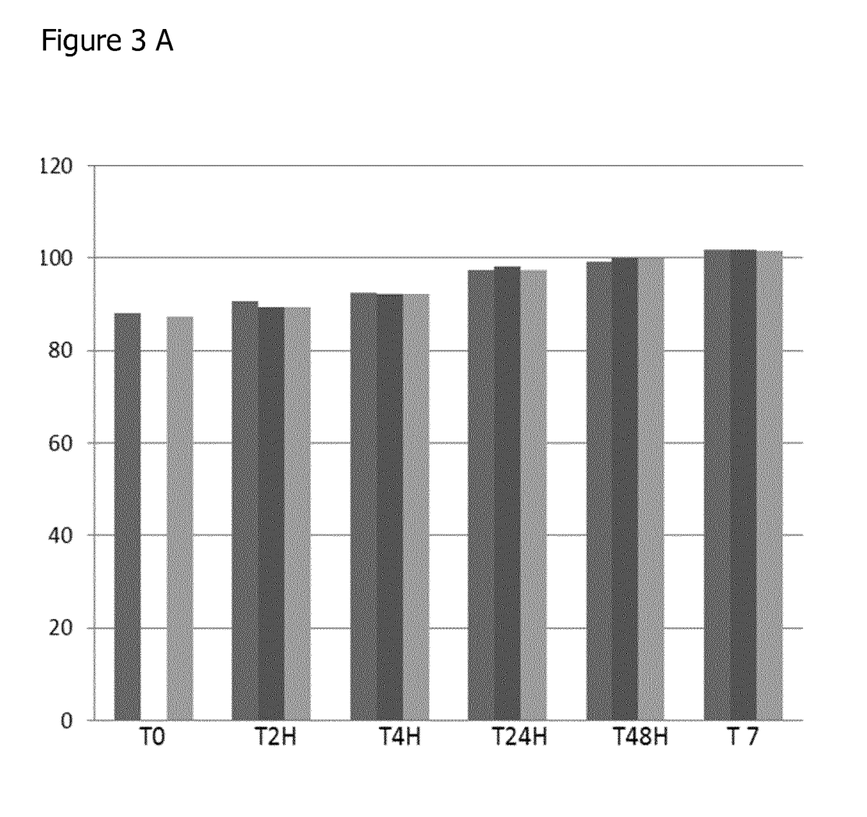
Figure 4:
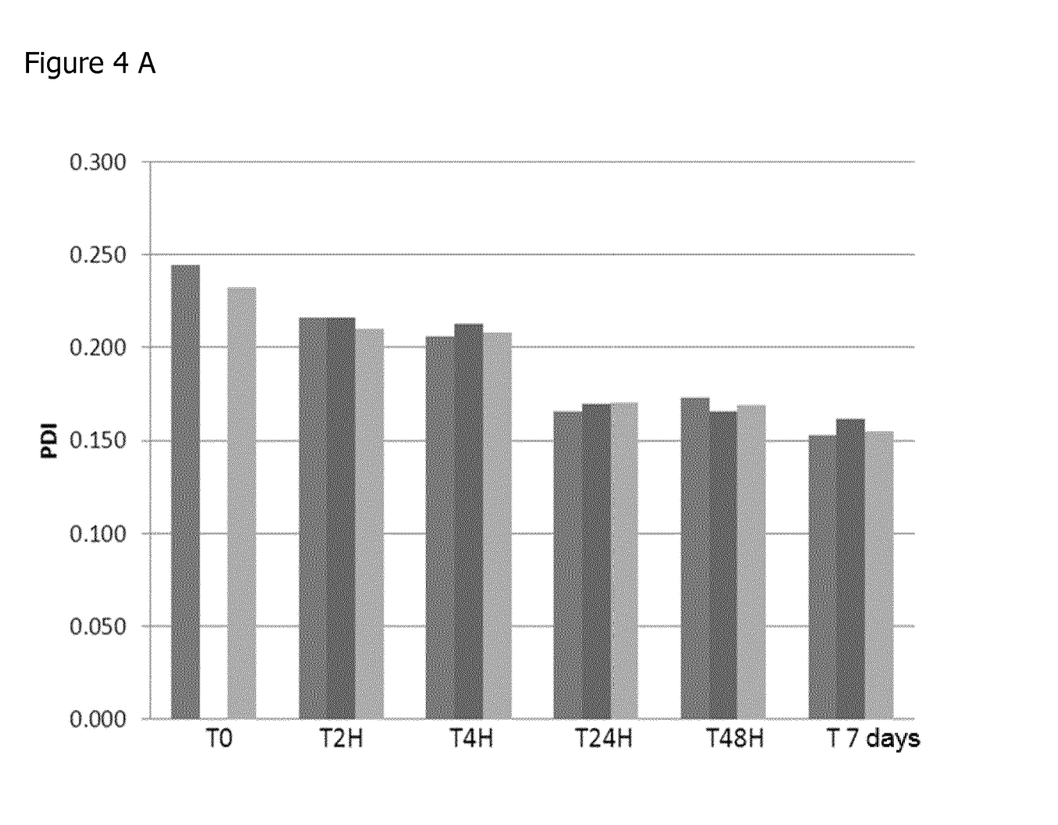
Figure 5:
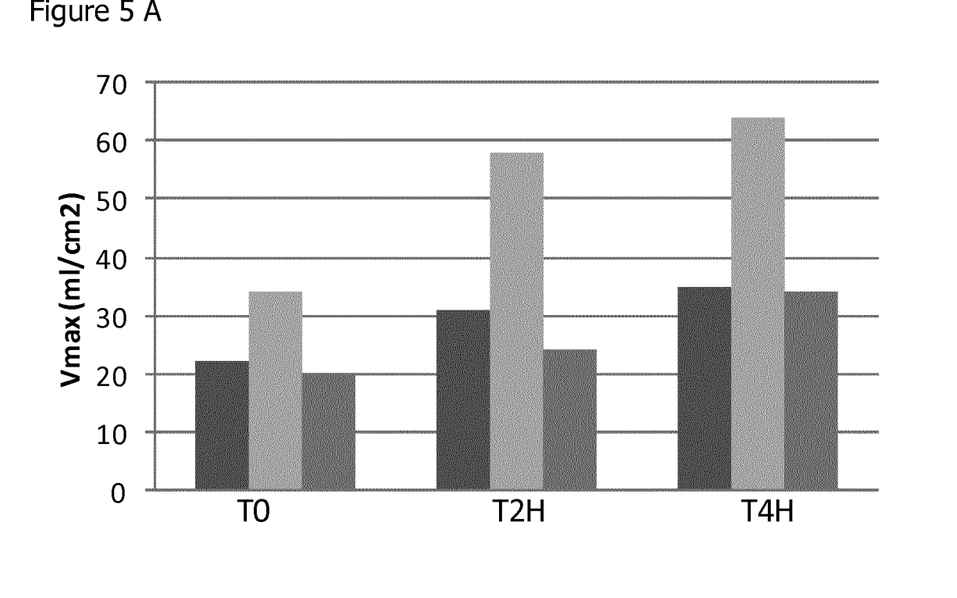
Figure 6:
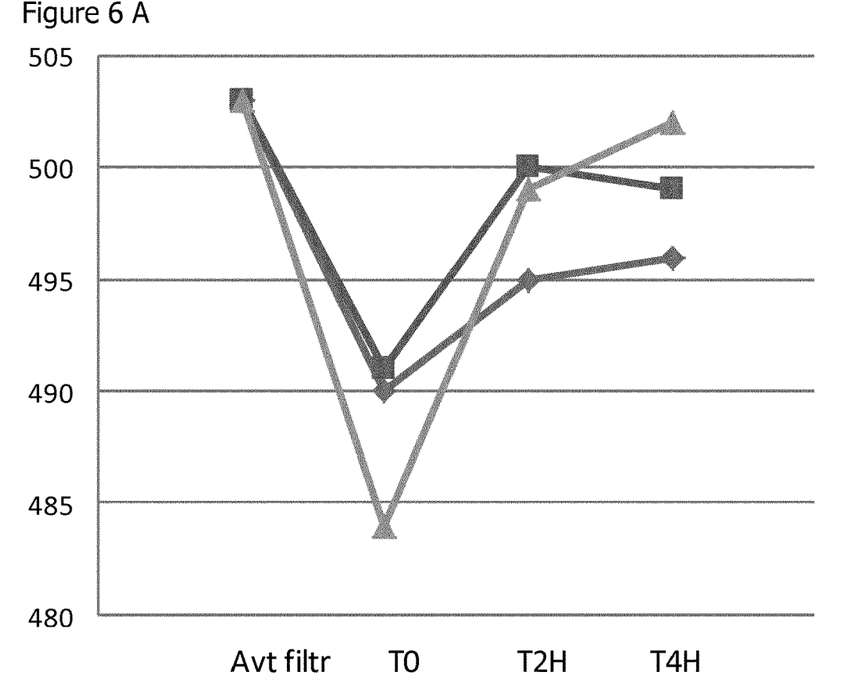

Results with respect to particle size (FIG. 3), PDI (FIG. 4), Vmax (FIG. 5) and Cholesterol content (FIG. 6) are presented in FIGS. 3 to 6. FIG. 3 (3A and 3B) displays that liposome size increases over the maturation time. FIG. 4 (4A and 4B) displays that, in parallel, the polydispersity (PDI) decreases over the maturation time because liposomes of smaller size disappear. Without wishing to be bound by a theory, it is believed that filterability is improved after maturation of the QS21 containing liposomes (as shown again in FIGS. 5A and 5B, wherein the Vmax increases over maturation time) because, in the absence of the maturation step, the presence of smaller liposomes may gradually accumulate into the pores of the filter and eventually result in the filter clogging.

Seq ID No. 1

```
  1 MGTVNKPVVG VLMGFGIITG TLRITNPVRA SVLRYDDFHI
    DEDKLDTNSV YEPYYHSDHA

61 ESSWVNRGES SRKAYDHNSP YIWPRNDYDG FLENAHEHHG
    VYNQGRGIDS GERLMQPTQM

121 SAQEDLGDDT GIHVIPTLNG DDRHKIVNVD QRQYGDVFKG
    DLNPKPQGQR LIEVSVEENH

181 PFTLRAPIQR IYGVRYTETW SFLPSLTCTG DAAPAIQHIC
    LKHTTCFQDV VVDVDCAENT

241 KEDQLAEISY RFQGKKEADQ PWIVVNTSTL FDELELDPPE
    IEPGVLKVLR TEKQYLGVYI

301 WNMRGSDGTS TYATFLVTWK GDEKTRNPTP AVTPQPRGAE
    FHMWNYHSHV FSVGDTFSLA

361 MHLQYKIHEA PFDLLLEWLY VPIDPTCQPM RLYSTCLYHP
    NAPQCLSHMN SGCTFTSPHL

421 AQRVASTVYQ NCEHADNYTA YCLGISHMEP SFGLILHDGG
    TTLKFVDTPE SLSGLYVFVV

481 YFNGHVEAVA YTVVSTVDHF VNAIEERGFP PTAGQPPATT
    KPKEITPVNP GTSPLIRYAA

541 WTGGLA
```

The invention claimed is:

1. A method of making a liposome composition comprising a saponin in a submicron liposomal formulation wherein the liposomes contain a lipid and a sterol, comprising the steps of:
   a) preparing a first submicron liposomal formulation wherein the liposomes contain a lipid and a sterol,
   b) adding the saponin to the first submicron liposomal formulation,
   c) maturing the saponin containing submicron liposomal formulation for at least 1, 2, 3, 4, 5, 6, 7, 8, 9, 10, 11, 12, 13, 14, 15, or, 16 hours, and,
   d) filtering the matured saponin containing submicron liposomal formulation of step c) through a sterile grade filter.

2. A method according to claim 1, wherein the first submicron liposomal formulation further contains a TLR-4 agonist.

3. A method according to claim 1, wherein the lipid is a neutral lipid.

4. A method according to claim 3 wherein the neutral lipid is a phosphatidylcholine selected from eggyolk phosphatidylcholine, dioleoyl phosphatidylcholine (DOPC) or dilauryl phosphatidylcholine.

5. A method according to claim 3, wherein the neutral lipid is DOPC.

6. A method according to claim 1, wherein the sterol is cholesterol.

7. A method according to claim 1, wherein the lipid to sterol ratio is between 3:1 and 5:1, such as about 4:1.

8. A method according to claim 1, wherein the saponin is QS21.

9. A method according to claim 2, wherein the TLR-4 agonist is a lipopolysaccharide.

10. A method according to claim 2, wherein the TLR-4 agonist is 3D-MPL.

11. A method according to claim 1, wherein the liposomal formulation is buffered at a pH between 5 and 7, such as at 6.1.

12. A method according to claim 1, wherein the liposomes following filtration of step d) have an Z-average diameter between 80 and 120 nm.

13. A method according to claim 1, further comprising step e) of filtering the submicron liposomal formulation of step d) through a further sterile grade filter.

14. A method according to claim 1, wherein the method further comprises a step of adding buffer to the submicron liposomal formulation of step a).

15. A method according to claim 1, wherein the filtering of step d) is performed at a temperature between 15 and 25° C.

16. A method according to claim 1, wherein the maturing of step c) is performed at a temperature below 15° C. such as between 2 and 8° C., and, the filtering of step d) is performed at a temperature between 15 and 25° C.

17. A method according to claim 1, wherein the maturing of step c) and the filtering of step d) are performed at a temperature between 15 and 25° C.

18. A method according to claim 1, wherein maturing is performed for at least 6 hours.

19. A method according to claim 1, wherein maturing is performed for no longer than 48 hours, no longer than 36 hours, or no longer than 24 hours.

20. A method according to claim 1, wherein maturing is performed for 16 to 24 hours.

21. A method according to claim 1, wherein maturing is performed at a temperature between 15 and 25° C. during 8 to 24 hours.

22. A method according to claim 1, wherein filtering is performed at a pressure between 1 and 1.5 bar.

23. A method according to claim 1, wherein the polydispersity index (PDI) of the saponin containing submicron liposomal formulation after maturation in step c) is lower than 0.225, or, lower than 0.200.

24. A method according to claim 1 wherein the, or, at least one sterile grade filter is a double layer filter of which the first layer has a larger pore size than the second layer filter.

25. A method according to claim 1, wherein the filtered composition is packaged into sterile glass vials or bags.

26. A method for preparing a vaccine composition comprising the method of claim 1 and combining the filtered composition with an antigen.

27. A method according to claim 26 wherein the vaccine is used in the prevention, attenuation or treatment of Malaria, Zoster, chronic obstructive pulmonary disease (COPD), CMV infection, RSV infection in elderly, HBV infection, HIV infection, Tuberculosis (TB), HSV infection, HPV infection, Staph, C Difficile, Community acquired pneumonia (CAP).

28. A method of preparing a vaccine kit comprising preparing the liposome composition according to claim 1 and packaging the liposome composition into a kit as a kit component in addition to an antigen kit component.

29. The method according to claim 28, wherein the antigen is lyophilised in a vial and the liposome composition is in a syringe.

30. A method of making a liposome composition comprising a saponin in a submicron liposomal formulation wherein the liposomes contain a lipid and a sterol, comprising the steps of:
    a) maturing a saponin containing submicron liposomal formulation wherein the liposomes contain a lipid and a sterol for at least 1, at least 2, at least 3, at least 4, at least 5, at least 6, at least 7, at least 8, at least 9, at least 10, at least 11, at least 12, at least 13, at least 14, at least 15, or at least 16 hours, and,
    b) filtering the matured saponin containing submicron liposomal formulation of step a) through a sterile grade filter.

31. The method according to claim 30, wherein the maturing of step a) is applied for 16 to 24 hours.

* * * * *